US010059981B2

(12) United States Patent
Jung et al.

(10) Patent No.: US 10,059,981 B2
(45) Date of Patent: *Aug. 28, 2018

(54) USE OF PERTURBANTS TO FACILITATE INCORPORATION AND RECOVERY OF TAGGANTS FROM POLYMERIZED COATINGS

(71) Applicant: APDN (B.V.I.) Inc., Tortola (VG)

(72) Inventors: Lawrence Jung, Dix Hills, NY (US); MingHwa Benjamin Liang, East Setauket, NY (US); James A. Hayward, Stony Brook, NY (US)

(73) Assignee: APDN (B.V.I.) INC., Tortola (VG)

( * ) Notice: Subject to any disclaimer, the term of this patent is extended or adjusted under 35 U.S.C. 154(b) by 317 days.

This patent is subject to a terminal disclaimer.

(21) Appl. No.: 15/079,214

(22) Filed: Mar. 24, 2016

(65) Prior Publication Data
US 2016/0362723 A1 Dec. 15, 2016

Related U.S. Application Data

(63) Continuation of application No. 13/648,594, filed on Oct. 10, 2012, now Pat. No. 9,297,032.

(51) Int. Cl.
C12Q 1/68 (2018.01)
C12Q 1/6806 (2018.01)

(52) U.S. Cl.
CPC ............ *C12Q 1/6806* (2013.01); *C12Q 1/68* (2013.01)

(58) Field of Classification Search
None
See application file for complete search history.

(56) References Cited

U.S. PATENT DOCUMENTS

| 4,548,955 | A | 10/1985 | Okhata et al. |
| 9,297,032 | B2 | 3/2016 | Jung et al. |
| 2005/0008762 | A1 | 1/2005 | Sheu et al. |
| 2008/0290649 | A1* | 11/2008 | Klein ............ B41M 3/144 283/86 |
| 2009/0075261 | A1 | 3/2009 | Hayward et al. |
| 2009/0136163 | A1 | 5/2009 | Kerr et al. |
| 2011/0165569 | A1 | 7/2011 | Macula |
| 2011/0229881 | A1* | 9/2011 | Oshima ............ B41M 3/14 435/6.1 |
| 2014/0256881 | A1 | 9/2014 | Berrada et al. |

FOREIGN PATENT DOCUMENTS

| JP | 2009517250 A | 4/2009 |
| WO | WO03038000 A1 | 5/2003 |

* cited by examiner

*Primary Examiner* — Samuel C Woolwine
(74) *Attorney, Agent, or Firm* — Hoffman & Barron, LLP

(57) ABSTRACT

The invention provides methods for increasing the recoverability of taggants from an object. The methods include the steps of incorporating a taggant into a solution; mixing the solution including the taggant with a perturbant to form a first perturbant taggant solution; mixing the first perturbant taggant solution with a polymer to form a second perturbant taggant polymer solution; and applying the second perturbant taggant polymer solution to at least a portion of the object to form a taggant-coated object. Methods for authentication of a taggant marked object are also provided.

19 Claims, No Drawings

USE OF PERTURBANTS TO FACILITATE INCORPORATION AND RECOVERY OF TAGGANTS FROM POLYMERIZED COATINGS

TECHNICAL FIELD

The present invention relates to methods for facilitating the inclusion of traceable taggants into polymers and for the recovery and detection of such taggants without altering the aesthetic appearance of the object or the matrix of the object.

BACKGROUND

Despite being composed of relatively simple nucleotide building blocks, nucleic acids are capable of encoding a vast array of information: witness the human genome encodes all the information necessary for the synthesis and assembly of all the components of the human body from the neural networks of the brain to the intricate structures of the skeleton, tissues and organs. Nucleic acids include deoxyribonucleic acid (DNA) and the more labile ribonucleic (RNA). Since nucleic acid sequences can be unique and complex, utilization of these particular characteristics in solving several common coding problems, such as authenticating and tracking products and detecting counterfeit products, has recently attracted great interest.

Many product manufacturers utilize apparent qualities and definitive designs identifiable as "trade dress" to uniquely identify their high quality and high value products and thereby earn the trust of their customers. Others also add labels for anti-counterfeit purposes. Traditional anti-counterfeiting labels are generally formed from materials having particularly targeted physical or chemical characteristics, for example, magnetic strips on checkbooks, laser holographs on credit cards, fluorescent ink on stock certificates, and heat-sensitive inks on confidential documents. Anti-counterfeiting labels have also been made by adding specific antigens to objects that need to be identified, the antigens can then be detected with an antibody specific for the antigen. However, antigens and antibodies are proteins with characteristically poor stability under many environmental conditions of temperature and humidity, and are prone to denaturation or even degradation and consequently lose activity and can easily be destroyed, thereby reducing the accuracy and reliability of identification.

Thus, nucleic acids, such as, for example, deoxyribonucleic acid (DNA) and ribonucleic acid (RNA) which encode essential hereditary information have been looked to as an improved alternative to commonly used anti-counterfeiting labels and markers. DNA and RNA are polymers consisting of a chain of nucleotides, referred to as "oligonucleotides" consisting of relatively short chains of up to say, twenty to fifty bases in length, or "polynucleotides" for longer chains. These oligonucleotide or polynucleotide chains consist of a number of nucleotides linked together in sequence like beads on a string. Each nucleotide consists of a ribose sugar-phosphate linked to one of only four kinds of nitrogenous bases: adenine (often represented in abbreviated form as "A"), guanine (represented as "G"), cytosine (represented as "C") and thymine (represented as "T") in the case of DNA; and adenine (A), guanine (G), cytosine (C) and uracil (U) in the case of RNA. The oligonucleotides or polynucleotides share the same sugar-phosphate backbone. The 3'-hydroxyl group on the ribose sugar is covalently bonded to the 5'-phosphate group of its neighboring nucleotide to form a chain structure with the planar nitrogenous bases protruding from the chain not unlike the teeth of a comb.

The bases A, T, G and C in one oligonucleotides or polynucleotides chain are each capable of specific-pairing with another base a different chain to form a double stranded structure, or with the same chain to form a double stranded loop or hairpin structure: Adenine specifically bonds with thymine through two hydrogen bonds in DNA (or with uracil in RNA) and cytosine specifically bonds with guanine through three hydrogen bonds. That is, T will bond to A and G to C bringing two nucleotide chains together to form a double strand, or two parts of a single nucleotide chain together to form a double stranded region with each strand of the duplex connected by a loop.

An additional advantage of nucleic acids for use as markers or taggants is that with the appropriate proper protection these molecules can be preserved for long periods of time. Evidence from preserved specimens in glaciers, ice sheets, tar pits and bogs and marshes shows that DNA is resilient to degradation over thousands, and in some cases millions of years. Such evidence has been used to deduce information concerning the ancestry and origins of ancient peoples as well as of plants and animals. Protected marker DNA can also be stabilized in polymers for coating of high value articles or objects of interest so as to survive long periods of time and can then used for identification, authentication and tracking purposes. This ability to persist over long periods of time coupled with very sensitive methods to detect low numbers of molecules for instance by amplification using the polymerase chain reaction (PCR), makes nucleic acids, and DNA in particular, an attractive candidate for use as a marker. Moreover, nucleic acids offer an almost unlimited coding capacity since the number of possible unique sequences increases fourfold with every additional base of the sequence of the oligonucleotide or polynucleotide.

Sheu et al. (U.S. Pat. No. 7,115,301) disclosed that DNA can be used to mark solid articles or substances by incorporating DNA into a variety of media that may be used for coating all or only part of an item of interest. Several media useful for such coatings disclosed by Sheu et al. include polycarbonate (PC), polymethyl methacrylate (PMMA), polystyrene (PS), and polypropylene (PP), or acrylic/epoxy resin-based formulations. Often times a non-invasive or non-destructive sampling method is required for tagging of precious articles, such as paintings or fragile articles, to preserve the aesthetic appearance and the integrity of the marked articles. However, the recovery of the taggant may be difficult or may provide such a low yield as to limit the applicability of the method.

Polymers such as acrylic or epoxy based resinous polymers can be used as the carrier media for taggants. Unfortunately, recovery of taggant from these polymers is often difficult and combinations of solvents have been developed to deal with such issues (see for instance, Elwell, U.S. Pat. No. 4,278,557). However, for most applications employing the use of such polymers as coatings, total dissolution of the polymer is not necessary (nor is it usually possible) in order to achieve adequate recovery of the taggant from the polymer coating for verification purposes. Furthermore, the use of such solvents on precious articles or objects to which the polymer is adhered may tarnish or damage the article or object and is undesirable and is usually discouraged. An owner or a bona fide purchaser interested in authentication of a purchase is unlikely to approve the use of significantly invasive or destructive methods.

Therefore, there is a need in the art for a system permitting retrieval of taggants from polymerized coating on an article of value without subjecting the tagged article to rigorous solvent treatments which may disturb the aesthetics of the article.

SUMMARY

Exemplary embodiments of the present invention provide a methodology for extraction of taggants from a tagged article surface without damaging the article or disturbing the aesthetics of its appearance.

In an exemplary embodiment of the present invention, a method for facilitating the inclusion of traceable taggants into a polymer matrix useful for coating an object is provided. The method includes incorporating a taggant into a solution, mixing the solution including the taggant with a perturbant to form a first perturbant taggant solution, mixing the first perturbant taggant solution with a polymer to form a second perturbant taggant solution and applying the second perturbant taggant solution to at least a portion of the object to form a taggant-coated portion of the object.

In another exemplary embodiment, the invention provides a method for increasing recoverability of traceable taggants incorporated into a polymer matrix in a coating of an object. The method includes incorporating a taggant into a solution, mixing the solution including the taggant with a perturbant to form a first perturbant taggant solution, mixing the first perturbant taggant solution with a polymer to form a second perturbant taggant solution and applying the second perturbant taggant solution to at least a portion of the object, wherein the recovery of the taggant is enhanced by the perturbant.

In still another exemplary embodiment of the present invention, a method for authenticating an object is provided. The method includes providing an object comprising a coating that includes a taggant such as a nucleic acid, a perturbant such as a polyol and a polymer coating; recovering the taggant from the object and verifying the authenticity of the object by identifying the taggant.

In accordance with another exemplary embodiment of the present invention, an object marked with a taggant is provided. The object can include a coating covering at least a portion of the surface of the object of interest; wherein the coating comprises a nucleic acid taggant and a perturbant in a polymer. Alternatively, the object can include a nucleic acid taggant and a perturbant in a polymer uniformly distributed throughout the object. In another alternative, the object may include the nucleic acid taggant and a perturbant in a polymer non-uniformly distributed in the object, such as in a portion of a coating and/or in a portion of the object that does not include a surface coating.

In accordance with yet another embodiment of the present invention, a method for authenticating an object is provided. The method includes providing an object having a coating that includes a taggant, at least one perturbant, such as a polyol, recovering the taggant from the object and verifying the authenticity of the object by identifying the taggant by any of the well known methods described in detail below.

In accordance with another embodiment of the present invention, an object marked with a taggant is provided. The marked object includes a coating comprising a nucleic acid taggant, at least one perturbant (such as a polyol) and a solvent; the coating may be cured and/or dried to provide a coated object incorporating a taggant and the polyol or polyols and any residual solvent after the curing and/or drying steps.

DETAILED DESCRIPTION

Definitions

The term "taggant" as used herein is used to denote a substance that is affixed to an object to indicate a property of the object, such as for instance its source of manufacture. The object to be marked with the taggant can be any solid traceable item, such as an electronic device, an item of clothing, paper, fiber, or fabric, or any other item of commerce, or cash or valuables, whether in storage or in transit. Alternatively, the item of commerce to be marked with the taggant can be a liquid, such as for instance an ink, a dye or a spray. In another alternative, the item of commerce can be a commodity item, such as paper, metal, wood, a plastic or a powder. The taggant can be, for example, specific to the company or the type of item (e.g. a model number), specific to a particular lot or batch of the item (lot number), or specific to the actual item, as in, for instance, a serial number unique to the item. In addition, the taggant can indicate any one or more of a variety of other useful items of data; for example, the taggant can encode data that indicates the name and contact information of the company that manufactured the tagged product or item, the date of manufacture, the distributor and/or the intended retailer of the product or item. The taggant can also indicate, for example and without limitation, component data, such as the source of the component incorporated into the item or the identity of the production plant or machinery that was used in the manufacture of the product or item; the date that the product or item was placed into the stream of commerce, the date of acceptance by the distributor and/or the date of delivery to the retailer and any other useful commercial, or other data such as for instance personal information of the owner of a custom made item. Each element of data or indicia can be encrypted or encoded in the taggant and can be deciphered from taggant recovered from the object and decoded or decrypted according to the methods described herein. The decoded or decrypted data can then be used to verify the properties of the object, or to authenticate the object, or to exclude counterfeit items.

The term "PCR" refers to a polymerase chain reaction. PCR is an amplification technology useful to expand the number of copies of a template nucleic acid sequence via a temperature cycling through melting, re-annealing and polymerization cycles with pairs of short primer oligonucleotides complementary to specific sequences bordering the template nucleic acid sequence in the presence of a DNA polymerase, preferably a thermostable DNA polymerase such as the thermostable Taq polymerase originally isolated from the thermophillic bacterium (*Thermus aquaticus*). PCR includes but is not limited to standard PCR methods, where in DNA strands are copied to provide a million or more copies of the original DNA strands (e.g. PCR using random primers: See for instance *PCR with Arbitrary Primers: Approach with Care*. W. C. Black IV, Ins. Mol. Biol. 2: 1-6, Dec. 2007); Real-time PCR technology, wherein the amount of PCR products can be monitored at each cycle (*Real time quantitative PCR*: C. A. Heid, J. Stevens, K. J. Livak and P. M. Williams, 1996 Genome Research 6: 986-994); Reverse transcription-PCR wherein RNA is first copied in DNA stands and thereafter the DNA strands are amplified by standard PCR reactions (See for example: *Quantitative*

*RT-PCR: Pitfalls and Potential*: W. F. Freeman, S. J. Walker and K. E. Vrana; BioTechniques 26:112-125, January 1999).

The term "monomer" as used herein refers to any chemical entity that can be covalently linked to one or more other such entities to form an oligomer or a polymer. Examples of "monomers" include nucleotides, amino acids, saccharides, amino acids, and the like.

The term "nucleic acid" means a polymer composed of nucleotides which can be deoxyribonucleotides or ribonucleotides. These compounds can be natural or synthetically produced deoxyribonucleotides or ribonucleotides. The synthetically produced nucleic acid can be of a naturally occurring sequence, or a non-natural unique sequence.

The terms "ribonucleic acid" and "RNA" denote a polymer composed of ribonucleotides. The terms "deoxyribonucleic acid" and "DNA" denote a polymer composed of deoxyribonucleotides.

The term "nucleotide" means a monomeric unit comprising a sugar phosphate, usually ribose-5'-phosphate or 2'-deoxyribose-5'-phosphate covalently bonded to a nitrogen-containing base, usually, adenine (A), guanine (G), cytosine (C), or thymine (T) in the case of a deoxyribonucleotide, and usually, adenine (A), guanine (G), cytosine (C), or uracil (U) in the case of ribonucleotides.

The term "oligonucleotide" as used in this specification refers to single or double stranded polymer composed of covalently nucleotide monomers forming a chain of from two to about twenty nucleotides in length.

The term "polynucleotide" as used in this specification refers to single or double stranded polymer composed of covalently nucleotide monomers forming a chain of generally greater than about twenty nucleotides in length.

Nucleic acids having a naturally occurring sequence can hybridize with nucleic acids in a sequence specific manner. That is they can participate in hybridization reactions in which the complementary base pairs A:T (adenine:thymine) and G:C (guanine:cytosine) form intermolecular (or intramolecular) hydrogen bonds and cooperative stacking interactions between the planar neighboring bases in each strand through Pi electrons, together known as Watson-Crick base pairing interactions. The bases of the nucleic acid strands can also hybridize to form non-Watson-Crick base pairs by so-called "wobble" interactions in which G (guanine) pairs with U (uracil), or alternatively, I (inosine) pairs with C (cytosine), U (uracil) or A (adenine).

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

Embodiments of the present invention are listed below as non-limiting examples illustrating the invention, but are not intended to be taken as limits to the scope of the present invention, which will be immediately apparent to those of skill in the art.

Exemplary embodiments provide methods for increasing the recoverability of a taggant from an object without disturbing the appearance of the object. Several exemplary embodiments of the present invention are described in detail below.

Exemplary embodiments of the present invention also provide methods for authenticating an object using taggants. For example, an exemplary embodiment of the invention provides a method for increasing the recoverability of a taggant from an object; the method includes incorporating a taggant into a solvent, mixing the solution including the taggant with a perturbant to form a first perturbant taggant solution, mixing the first perturbant taggant solution with a polymer to form a second taggant solution and applying the second taggant solution to at least a portion of the object to form a taggant-coated portion of the object. The taggant can be soluble in an aqueous solution. Examples of an aqueous soluble taggant include nucleic acids, saccharides, peptides and many proteins. Alternatively, the taggant can be insoluble in an aqueous solution, or an organic solvent. Examples of a taggant that is insoluble in aqueous solutions or organic solvents include particulate taggants, such as for instance, a up-converting phosphor (UCP) taggant, which may be any suitable UCP taggant, such as a nucleic acid-linked UCP.

An exemplary embodiment of the invention further provides a method for increasing the recoverability of a taggant from an object; the method includes incorporating a taggant in an solution, mixing the solution including the taggant with a perturbant to form a first perturbant taggant solution, mixing the first perturbant taggant solution with a polymer to form a second taggant solution and applying the second taggant solution to at least a portion of the object to form a taggant-coated portion of the object. The solution into which the taggant is incorporated can be an aqueous solution or an organic solvent.

The polymer useful as coatings in the practice of the present invention for incorporating recoverable taggants into coatings of objects of interest can be any polymer that can be used to form a coating on an object, such as for example, epoxy-acrylate, epoxy-urethane, polycarbonate (PC), polymethyl methacrylate (PMMA), polyurethane (PU), polystyrene (PS), polyamides (e.g. nylon 6, nylon 66), polypropylene (PP), polyvinyl chloride (PVC), polysulphones, polyvinylacetate (PVA), polyester (PES), polyethylene terephthalate (PET), polyethylene (PE), benzocyclobutene (BCB), high-density polyethylene (HDPE), polyvinylidene chloride (PVDC), low-density polyethylene (LDPE), high impact polystyrene (HIPS), acrylonitrile butadiene styrene (ABS), phenolics (PF), melamine formaldehyde (MF), polyetheretherketone (PEEK), polyamides, polyetherimide (PEI), polyimide, polyether imide, polyether ketone imide, polylactic acid (PLA), polytetrafluoroethylene (PTFE), polymethyl pentene, polyether ketone, polyether sulphone (PES), polyphenylene sulfide, polytetrafluoroethylene, butyl rubber, fluropolymers, silicones, Ionomers, moldable elastomers, ethylene vinyl alcohol (EVOH), methalocene polymers and polyethylene naphthalate.

In addition, other polymers into which a taggant can be incorporated according to the methods of the present invention and which can also be used for coating all or part of the surface of an object include, for example, acrylic compounds such as polymethyl methacrylate (PMMA), a transparent thermoplastic synthetic polymer of methyl methacrylate, also called acrylic glass; and acrylic copolymers such as polymethyl methacrylate-polyacrylonitrile copolymers; and the thermosetting epoxy-based polymer compounds such as epoxy-copolymers formed by polymerization of a resin compound and a hardener or activator. The resin is a monomer or short chain having an epoxy group at each terminus. For example a commonly used epoxy resin is formed by a reaction between a reactive epoxide such as epichlorohydrin (a.k.a. glycidyl chloride and 1-chloro-2,3-epoxypropane) and a reactive aromatic compound, such as bisphenol-A. An example of a commonly used hardener is triethylenetetramine (TETA), although almost any polyamine can be substituted. Alternatively, a mixture of two or more of any of the foregoing acrylic compounds and epoxy-based compounds can be used for the coating according to an embodiment of the present invention.

In another exemplary embodiment, the epoxy-based compound that includes the taggant of the present invention can include compounds and resins having two or more epoxy groups. These compounds may be in liquid, gel-like or in solid form. For example, epoxy-based compounds useful in the practice of the present invention include epoxy resins such as: glycidyl ethers obtained by reacting epichlorohydrin with a polyhydric phenol such as bisphenol A, bisphenol F, bisphenol S, hexahydrobisphenol A, tetramethylbisphenol A, diallyl-bisphenol A, hydroquinone, catechol, resorcin, cresol, tetrabromobisphenol A, trihydroxybiphenyl, benzophenone, bisresorcinol, bisphenol hexafluoroacetone, tetramethylbisphenol A, tetramethylbisphenol F, tris (hydroxyphenyl)methane, bixylenol, phenol-novolac, or cresol-novolac; polyglycidyl ethers obtained by reacting epichlorohydrin with an aliphatic polyhydric alcohol such as glycerin, neopentyl glycol, ethylene glycol, propylene glycol, butylene glycol, hexylene glycol, polyethylene glycol, or polypropylene glycol; glycidyl ether esters obtained by reacting epichlorohydrin with a hydroxycarboxylic acid such as p-hydroxybenzoic acid or β-hydroxynaphthoic acid; polyglycidyl esters obtained from polycarboxylic acids such as phthalic acid, methylphthalic acid, isophthalic acid, terephthalic acid, tetrahydrophthalic acid, hexahydrophthalic acid, endomethylene tetrahydrophthalic acid, endomethylene hexahydrophthalic acid, trimellitic acid, and polymerized fatty acids; glycidylamino-glycidyl ethers obtained from aminophenols and aminoalkylphenols; glycidylamino-glycidyl esters obtained from aminobenzoic acids; glycidylamines obtained from aniline, toluidine, tribromoaniline, xylylenediamine, diamino cyclohexane, bisaminomethyl-cyclohexane, 4,4'-diaminodiphenyl methane, and 4,4'-diaminodiphenyl sulfone; and epoxydized polyolefins.

In an exemplary embodiment, the acrylic compound of the polymer for incorporation of the taggant according to the present invention can be, for example, an acrylate compound, an acrylate polymer, an acrylic fiber, an acrylic paint, an acrylic resin, an acrylic glass, or the like.

In an exemplary embodiment of the present invention, the polymer is for example, a natural polymer, a varnish, a polyurethane, a shellac or a lacquer. The varnish, polyurethane, shellac or lacquer can be any suitable varnish, polyurethane, shellac or lacquer, such as for instance and without limitation, a polyurethane varnish from Minwax® Co., Upper Saddle River, N.J. Alternatively the polymer useful as a coating can be a natural polymer, such as beeswax, e.g. the beeswax available from Mountain Rose Herbs, Eugene, Oreg.

In another exemplary embodiment, the polymer is a component of a polymer-containing composition, such as for example, a printing ink. For example, in an exemplary embodiment, the ink may be a heat-curing epoxy-acrylate ink, such as Product No. 4408R or the 970 series Touch Dry® pellet each from Markem®, Keene, N.H. Alternatively, the Artistri® P5000+Series-Pigment Ink sold by Dupont® or an Epoxy Acrylate Ink, such as Product No. 00-988, Rahn USA Corp. can be used.

The taggants of the present invention include, for example, nucleic acid taggants. Nucleic acid is a general term for deoxyribonucleic acid (DNA) or ribonucleic acid (RNA), and can be synthetic, or derived from an animal, a plant, a bacterium, a virus, a fungus, or a synthetic vector or a fragment of any of the above-listed nucleic acids, etc. It should be noted that a synthetic nucleic acid can have a sequence of a naturally occurring nucleic acid of an animal, plant, bacterium, fungus, virus or any other organism or synthetic vector. Alternatively, a synthetic nucleic acid can have a unique sequence not found in nature. It should be understood that such unique non-natural sequences may have stretches of sequences which are found in nature, but the entire non-natural sequence is unique and is not found in any plant, animal or virus or any other natural organism. In particular, the nucleic acid sequence encoding the element of data or indicia encrypted or encoded in the taggant of the invention is a unique, non-natural sequence and thereby is adapted for use in authentication of an object of interest.

The taggant useful in the practice of the present invention can be any suitable detectable or traceable taggant, for example, a chemical marker or a biological marker. In an embodiment of the methods of the present invention, the taggant is selected from a UV fluorophore, a ceramic IR marker, DNA, an amino acid, a peptide, a protein, a lipid, a sugar, a polysaccharide, a pheromone, a scent, a trace element, a rare earth element, or a combination of any two or more thereof.

In an embodiment of the present invention, the taggant includes a nucleic acid. In one embodiment, the taggant consists essentially of DNA and no other significant component useful for identification or authentication.

In addition, other taggants such as, for example, ultraviolet (UV) taggants, Up Converting Phosphor (UCP) infrared (IR) taggants, UV marker taggants, UV fluorophore taggants, ceramic IR marker taggants, protein taggants, and/or trace element taggants can be used in combination with nucleic acid taggants. In an exemplary embodiment, the taggants used may include, for example, a combination of DNA taggants, and an IR upconverting phosphor (UCP) taggant. Alternatively, in another exemplary embodiment, the taggants used may include, for example, a combination of DNA taggants, an IR upconverting phosphor (UCP) taggant and a UV taggant. For example, in an exemplary embodiment, the IR (UCP) taggant can be, for example, a green, a blue or a red (UCP) IR taggant, such as for instance the Green IR Marker, Product No. BPP-1069; the Blue UCP, Product No. BPP-1070; or the Red UCP, Product No. BPP-1071 from Boston Applied Technologies Inc., Woburn, Mass.

The solution in which the soluble taggants are dissolved according to the methods of the present invention can include, for example, water, TE buffer (10 mM Tris•HCl, 1 mM EDTA), Tris-glycine buffer, Tris-NaCl buffer, TBE buffer (Tris-borate-EDTA), TAE buffer (Tris-acetate-EDTA) and TBS buffer (Tris-buffered saline), HEPES buffer (N-(2-Hydroxyethyl)piperazine-N'-ethanesulfonic acid), MOPS buffer (3-(N-Morpholino)propanesulfonic acid), PIPES buffer (Piperazine-N,N'-bis(2-ethanesulfonic acid), MES buffer (2-(N-Morpholino)ethanesulfonic acid), PBS (Phosphate Buffered Saline), PBP buffer (sodium phosphate+EDTA), TEN buffer (Tris/EDTA/NaCl), TBST buffer (Tris-HCl, NaCl, and Tween 20), PBST buffer (Phosphate Buffered Saline with Tween 20) and any of the many other known buffers used in the biological and chemical sciences.

In an exemplary embodiment the perturbant useful for the practice of the present invention can be any suitable perturbant, such as a polyol or a diol or glycol, a starch or a pyrrolidone. The polyol can be any suitable polyol, such as a polyethylene glycol polymer, for instance a PEG 200 i.e. a polyethylene glycol having an average molecular number of 200 ethylene glycol units per chain (such as the PEG200

$M_n$ 200 Product No. P3015), Sigma-Aldrich, St. Louis, Mo. Alternatively, in another embodiment, the polyethylene glycol can be a PEG 10,000 polyol polymer such as the PEG10,000 Product No. P3015, $M_n$ 10,000 from Sigma-Aldrich.

In another embodiment, the glycol useful as a perturbant according to the invention can be any suitable glycol or diol, such as for instance, ethylene glycol, diethylene glycol, glycerol, methanediol, triethylene glycol, propylene glycol from Sigma-Aldrich, or 1,2-butanediol or 1,4-from butanediol from Fluka Analytical.

In another embodiment, the starch can be for example a hydroxylpropyl starch such as Zeina® B860 from Grain Processing Corp., Muscatine, Iowa. In still another embodiment, the pyrrolidone perturbant of the invention can be any suitable pyrrolidone such as for instance an N-alkyl pyrrolidone, or the caprylyl pyrrolidone surfactant: Surfadone® LP100 available from Ashland Inc., Covington, Ky.

In an exemplary embodiment, the perturbant of the present invention can be used in a solution containing the polymer and the taggant in an amount of about 0.1% to about 30% w/w of the taggant in the solution. In another exemplary embodiment, the perturbant of the present invention can be used in a solution containing the polymer and the taggant in an amount of about 1% to about 25% w/w of the taggant in the solution. Alternatively, the perturbant of the present invention can be used in a solution containing the polymer and the taggant in an amount of about 5% to about 20% w/w of the taggant in the solution. In another exemplary embodiment, the perturbant of the present invention can be used in a solution containing the polymer and the taggant in an amount of about 7% to about 15% w/w of the taggant in the solution. In still another exemplary embodiment, the perturbant of the present invention can be used in a solution containing the polymer and the taggant in an amount of about %10 w/w of the taggant in the solution.

Alternatively, in one exemplary embodiment, the perturbant of the present invention can be used in a solution containing the polymer and the taggant in an amount of about 0.1% to about 30% w/w of the taggant in the solution. In another exemplary embodiment, the perturbant of the present invention can be used in a solution containing the polymer and the taggant in an amount of about 5% to about 30% w/w of the taggant in the solution. Alternatively, the perturbant of the present invention can be used in a solution containing the polymer and the taggant in an amount of about 10% to about 30% w/w of the taggant in the solution.

In one exemplary embodiment, the perturbant of the present invention can be used in a solution containing the polymer and the taggant in an amount of about 1% to about 25% w/w of the taggant in the solution. In an exemplary embodiment, the perturbant of the present invention can be used in a solution containing the polymer and the taggant in an amount of about 1% to about 20% w/w of the taggant in the solution. In an exemplary embodiment, the perturbant of the present invention can be used in a solution containing the polymer and the taggant in an amount of about 1% to about 15% w/w of the taggant in the solution. In an exemplary embodiment, the perturbant of the present invention can be used in a solution containing the polymer and the taggant in an amount of about 1% to about 10% w/w of the taggant in the solution.

Without wishing to be bound by theory, it is believed that the perturbants of the present invention create microcrevices and micropockets and microenvironments in the polymerized polymer facilitating recovery of the taggant (e.g. a DNA taggant) more efficiently than from polymerized coatings lacking such perturbants.

The objects of interest coated with the taggants according to exemplary embodiments of the present invention include, for example, ceramic surfaces, plastic films, vinyl sheets, antiques, items of jewelry, identification cards, credit cards, magnetic strip cards, paintings, artwork, souvenirs, sports collectibles and other collectibles. The authenticity of these objects can then be verified by recovering and identifying the taggants coated thereon through, for example, methods described in further detail below.

The coating that includes or incorporates a taggant of the invention which can be applied to an object of interest can be any suitable coating which is stable and capable of incorporating the taggant, for example, a plastic, a varnish, a polyurethane, a shellac or a lacquer. Alternatively, the coating can be beeswax.

Alternatively, the coating of the present invention applied to an object of interest can be, for example, an ink, a paint, a sealer, a glue, a coating containing one or more dyes, one or more dyestuffs, or one or more pigments, and other such common coatings.

In another embodiment of the present invention, the method comprises incorporating or dissolving the taggant in a solution to form a taggant solution prior to mixing the nucleic acid taggant with the perturbant, mixing the first solution with a polymer to form a second solution, and applying the second solution to at least a portion of the object to form a taggant-coated portion of the object, wherein the taggant is recoverable from the object.

In one embodiment, the second solvent, is a non-polar solvent. In one embodiment, the second solvent is selected from the group consisting of methyl ethyl ketone (MEK), acetone, an alcohol, such as for instance methanol, ethanol, n-propanol, isopropanol, n-butanol, or isobutanol etc. or an ether, such as for instance dimethylether, methylethyl ether and diethyl ether etc. Alternatively, the second solvent can be a combination of two or more ketones, alcohols, or ethers. In another alternative the second solvent can be a combination of any two or more of the above solvents.

In another embodiment, the taggant includes an IR upconverting phosphor (UCP) taggant and a DNA taggant, and wherein the perturbant is a polyol.

In still another embodiment, the polymer is a varnish, a polyurethane, a shellac or a lacquer.

In one embodiment of the present invention, the solution enhancer includes at least one polyol. The polyol can be any suitable polyol, such as for ethylene glycol, diethylene glycol, glycerol, methanediol, 1,2-butanediol, 1,4-butanediol, triethylene glycol, propylene glycol, and polyethylene glycol (PEG). The polyethylene glycol can be of any suitable size, such as for instance and without limitation, PEG 200, PEG 400, PEG 600, PEG 2000, PEG 3350 or PEG 10,000.

For example, the polyethylene glycol may be any suitable polyethylene glycol available from Sigma-Aldrich, St. Louis, Mo. The PEG200 may be, for example $M_n$ 200, Product No. P3015. The PEG 400 may be, for example, $M_n$ 400, Product No. 202398. The PEG600 may be, for example, $M_n$ 600 waxy moist solid, Product No. 202401. The PEG2,000 may be, for example, $M_n$ 1900-2200 solid flakes, Product No. 295906-250G. The PEG3350 may be, for example, $M_n$ 3000-3700, Product No. 83272. In another exemplary embodiment, the PEG10,000 may be, for example, $M_n$ 10,000, Product No. 309028.

In another embodiment, the polymer is selected from the group consisting of polycarbonate (PC), polymethyl methacrylate (PMMA), polyurethane (PU), polystyrene (PS), nylon or polypropylene (PP) all of which are readily commercially available. In another embodiment, the polymer includes a first solvent comprising a polymeric compound the polymerization of which can be initiated and hardened by heat, UV or a catalyst.

In one embodiment, the method of the present invention further includes curing or drying the second solution applied on the object to provide a coating including the taggant. The coating can be over all or part of the object to be identified, validated, authenticated, or tracked.

After coating an object with the taggant-containing polymer according to the methods of the present invention, the coating can be, dried or cured such that the coating adheres to the object, thereby providing the object with authentication, tracking and anti-counterfeiting functions.

In exemplary embodiments of the present invention, the taggant can be recovered from the taggant-coated portion of the object without disturbing the appearance of the object. For example, the taggant can be recovered from the taggant-coated portion of the object by swabbing a surface of the object. In one exemplary embodiment, the object may be swabbed with a cotton swab, a cotton ball, a cotton fabric, a filter or a tissue paper, or any other suitable sampling medium. For example, in an exemplary embodiment the taggant is recovered from the taggant-coated portion of the object using any suitable solvent on an applicator such as a cotton-tipped applicator. The solvent can be any suitable solvent available from reagent vendors such as Sigma-Aldrich. Suitable solvents include, for instance, ethanol, methanol, propanol, toluene, xylene and methylethylketone (MEK, 2-butanone), to name but a few. Other suitable commonly available solvents will be readily identifiable by those of skill in the art.

In an embodiment of the invention, the polymer into which the polymer into which the first solution containing the solution enhancer and taggant is mixed, can be gasoline, diesel fuel, such as the gasoline or diesel fuel, a lubricant oil such as motor oil, heating oil, kerosene, jet fuel or unrefined crude oil, and the like.

Exemplary embodiments of the present invention also provide a method for authenticating an object which includes providing an object comprising a coating comprising a taggant, a perturbant and a polymer, recovering the taggant from the object for identification, tracking, or verifying the authenticity of the object by identifying the unique taggant. In one embodiment, the unique taggant is a DNA taggant having a unique DNA sequence and the unique non-natural DNA sequence is stored in a database that matches the unique DNA sequence to the data elements corresponding to the object which is coated with the unique taggant. The database can in turn be located on a computer that can be accessed in order to locate, track, authenticate and verify the identity of the tagged object from which the taggant was recovered.

DNA taggants useful in the examples described below include any suitable DNA taggant, such as for instance, in one embodiment, the DNA taggant is a double stranded DNA oligomer having a length of between about 40 base pairs and about 1000 base pairs. In other embodiments the DNA taggant is a double stranded DNA oligomer with a length of between about 80 and 500 base pairs. In another embodiment the DNA taggant is a double stranded DNA oligomer having a length of between about 100 and about 250 base pairs. Alternatively, the DNA taggant can be single-stranded DNA or any suitable length, such as between about 40 bases and about 1000 bases; between about 80 and 500 bases; or between about 100 and about 250 bases. The DNA taggant can be natural DNA, whether isolated from natural sources or synthetic; or the DNA taggant can be a synthetically produced non-natural sequence. All or a portion of the DNA may comprise an identifiable sequence.

In one exemplary embodiment, the DNA taggant is identifiable by any suitable detection and/or identification method such as for example, hybridization with a taggant-sequence specific nucleic acid probe, an in situ hybridization method (including fluorescence in situ hybridization: FISH), amplification using a polymerase chain reaction (PCR), such as quantitative/real time PCR and detection of the amplified sequences (amplicons) by any of the variety of standard well known methods.

For example, in the PCR identification method, the nucleic acid taggants, e.g., DNA taggants recovered from the object are amplified by polymerase chain reaction (PCR) and resolved by gel electrophoresis. Since the sequence of the nucleic acid taggants of the present invention are unique and specific to the tagged object, the original nucleic acid will be amplified only by use of primers having specific sequences complementary to a portion of the unique taggant sequence. Through this procedure, if the examined object carries the original nucleic acid, the PCR procedure will amplify extracted nucleic acid to produce amplicons of a predetermined size and a sequence identical to a portion of the original nucleic acid sequence of the taggant. In contrast, if the sample recovered from the examined object does not include the unique nucleic acid corresponding to the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is vanishingly small. Therefore, by comparing the sizes of PCR products, the authenticity of labeled objects can be verified, non-authentic objects can be screened and rejected and anti-counterfeit screening purpose is then achieved.

The number of amplicons amplified and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels and the electrophoretic separation can be in a slab gel or by capillary electrophoresis.

EXAMPLES

It should be understood that following examples set forth are intended to be illustrative only and that exemplary embodiments of the present invention are not limited to the conditions or materials recited therein.

The following examples illustrate embodiments of the present invention to enhance recoverability of a taggant from a taggant coating on a coated object according the following method: incorporating or dissolving a taggant into an solution, mixing the taggant solution with a perturbant to form a first perturbant taggant solution; then mixing this perturbant taggant solution with a polymer to form a perturbant taggant polymer solution; and coating at least a portion of the object to form a taggant-coated object.

Example 1

Inclusion of UV Taggant and DNA Taggant in Solvent Based Topcoat Varnish and the Recovery of the DNA Taggant Five percent solution (w/w) of UV taggant and DNA taggant at 1 ng/ml final concentration are first mixed together and sufficient Surfadone®LP100 is added to reach a concentration of 7% of final volume (v/w) before adding to 1 L of varnish. The mixture is paddle blended for 10 min and applied onto plastic film to dry in an oven at 60° C. overnight. The varnish film is sampled using a cotton swab dipped in 30% EtOH solution and swabbed across the varnished surface several times. UV taggant is picked up by the swab without disturbing the appearance of the varnish and the extracted sample transferred by the swab is used for DNA authentication.

Example 2

Inclusion of Up Converting Phosphor (UCP) IR and DNA Taggants in Polyurethane Varnish and Recovery Thereof Five percent (w/w) of UCP IR and DNA taggant (which may be in the form of a DNA-linked UCP taggant) at 5 ng/ml final concentration are first mixed together and added to 10 g molten PEG10,000 (average molecular no: $M_n$ 10,000, Product No. 309028, Sigma-Aldrich) before adding to 1 L of polyurethane varnish (Minwax® Co., Upper Saddle River, N.J.). The mixture is then paddle blended for 10 min and applied onto vinyl sheet(s) to dry in 60° C. oven for 1 hour. The varnished film is sampled by using a cotton swab (Cotton tipped Applicator No. 25-826 5WC Puritan Medical Products, Guilford, Me.) dipped in 100% MEK solution and swabbed across the varnished surface for several times. UCP-linked DNA taggant is picked up by the swab without disturbing the appearance of the object, and the DNA is then authenticated by PCR-based analysis.

Example 3

Inclusion of Particulate DNA Taggants in Natural Varnishes Such as Shellac and the Recovery Thereof DNA taggant at 5 ng/ml final concentration is added to 10 g PEG 200 before adding to 1 L of varnish. The mixture is paddle blended for 10 minutes and applied onto a plastic film and allowed to cure at room temperature. The varnish film is then sampled by using a cotton swab dipped in 20% EtOH (Sigma-Aldrich) and swabbed across the varnished surface several times. The DNA taggant is picked up by the swab without disturbing the appearance of the varnish, and the DNA is then authenticated by PCR based analysis.

Example 4

Inclusion of UCP IR and DNA Taggants in Heat Cured Printing Ink and the Recovery Thereof Ten percent (w/w) of UCP IR taggant linked DNA taggant at 10 ng/ml final concentration are first mixed together and added to 5% g hydroxypropyl starch before adding to 1 L of printing ink. The mixture is then blended for 10 min and used for the printing on ceramic surfaces and dried in 120° C. oven for 24 hours. The dried ink is sampled by using a cotton swab dipped in 100% MEK and swabbed across the printed surface several times. The UCP-linked taggant is picked up by the swab without disturbing the appearance of the print, and the DNA is then authenticated utilizing a PCR-based assay.

Example 5

Inclusion of UCP IR and DNA Taggants in UV Cured Printing Ink and the Recovery Thereof Five percent (w/w) of UCP IR taggant and DNA taggant are first mixed together and added to 50 g of melted PEG 10,000 before being adding to 1 L of printing ink. The mixture is then paddle blended for 10 min and printed on ceramic surfaces and subjected to high intensity mercury lamp for 5 sec. to cure. The cured ink is then sampled using a cotton swab dipped in 100% MEK solution and swabbed across the printed surface several times. The UCP taggant is picked up by the swab without disturbing the appearance of the print, and the DNA is then authenticated by utilizing a PCR based assay.

Example 6

Inclusion of DNA Taggants in a Two Component Glue System and Recovery Thereof

One of the components of the two component glue system acts as catalyst to cure the glue. One percent (w/w) of UCP IR taggant, one percent (w/w) UV marker, and DNA taggant at 20 ng/ml final concentration are first mixed together and added to 50 g of propylene glycol before adding to 1 L of one or both components (resin and hardener) of the glue. Two components of the glue are then mixed and allowed to cure. The cured glue is then sampled using a cotton swab dipped in 100% MEK and swabbed across the printed surface several times. The taggant is picked up by the swab without disturbing the appearance of the cured glue block, and the DNA is then authenticated by PCR assay.

Example 7

Inclusion of Up Converting Phosphor (UCP) IR and DNA Taggants in Polyurathane Varnish and the Recovery Thereof Five percent (w/v) of UCP IR taggant (e.g. ADA-3253 from H.W. Sands Corp., Jupiter, Fla.) and DNA taggant at 5 ng/ml final concentration are first mixed together and added to 50 ppm of ethylene glycol before adding to 1 L of solvent-based polyurethane varnish. The mixture is then blended and applied onto vinyl sheet(s) to cure under an infrared light station for five minutes. The varnished film is sampled by using a cotton swab dipped in 100% EtOH and swabbed across the varnished surface several times. UCP taggant is picked up by for DNA authenticated by PCR-based analysis.

Example 8

Inclusion of UV Taggant and DNA Taggant in Solvent Based Topcoat Varnish and the Recovery Thereof Five percent (w/v) of water soluble UV taggant and DNA taggant at 1 ng/ml final concentration are first mixed together and added to 5% of PEG2,000 to the final volume (w/v) before adding to 1 L of MEK based varnish. The mixture is paddle blended for 10 min and applied onto plastic film to dry in 60° C. oven overnight. The varnish film is sampled by using a cotton swab dipped in 30% EtOH solution and swabbed across the varnished surface several times. UV taggant along with the DNA taggant is picked up by the swab without disturbing the appearance of the varnish, and the swab is then used for DNA authentication.

Example 9

Inclusion of UCP IR and DNA Taggants in UV-Cured Printing Ink and the Recovery Thereof Five percent (w/v) of UCP IR taggant and DNA taggant at 10 ng/ml final concentration are first mixed together and added to 25 mL of PEG400 before being added to 1 L of MEK-based printing ink. The mixture is then paddle blended for 10 min and used for printing on epoxy surfaces and subjected to heat from a high intensity mercury lamp for 1 minute to cure. The cured ink is then sampled using a cotton swab dipped in 100% Ether and swabbed across the printed surface several times. The UCP taggant is picked up by the swab without disturbing the appearance of the print, and the DNA is authenticated by a PCR-based assay.

Example 10

Inclusion of Particulate DNA Taggants in Varnish or Shellac and the Recovery Thereof DNA taggant at 5 ng/ml final concentration is added to 10 g glycerol before adding to 1 L of varnish (Minwax® Co., Upper Saddle River, N.J.). The mixture is paddle blended for 10 minutes and applied onto a plastic film for room temperature curing. The varnish film is then sampled using a cotton swab dipped in 100% acetone and swabbed across the varnished surface several times. The DNA taggants are picked up by the swab without disturbing the appearance of the varnish, and the DNA is then authenticated by a PCR-based assay.

Example 11

Inclusion of DNA Taggants in Lubricant and the Recovery Thereof 10 ng/ml (final concentration) DNA taggant at is mixed with 100 uL PEG400 average $M_n$ 400, Product No. 202398, Sigma-Aldrich) before incorporation of 1 L of lubricant (Havoline® motor oils sold by Chevron USA). The DNA is purified from the lubricant and the DNA is then authenticated utilizing a PCR-based assay.

Example 12

Inclusion of DNA Taggants in Beeswax and the Recovery Thereof 10 ng/ml of DNA taggant (final concentration) is added to 100 ppm of molten PEG3350 average $M_n$ 3000-3700, Product No. 83272, Sigma-Aldrich) before being added to 1 L of molten beeswax (Mountainroseherbs.com, Eugene, Oreg.) The DNA is purified from the wax and the DNA is then authenticated by utilizing a PCR based assay Example 13

Inclusion of DNA Taggants in Solvent-Based Inkjet Inks and Recovery Thereof 10 ng/ml of DNA taggant (final concentration) is added to 1% of PEG200 average $M_n$ 200, Product No. P3015, Sigma-Aldrich) before being mixed into 1 L of a solvent based inkjet ink (such as the 970 series Touch Dry® pellet; or the 4408R heat-curing ink sold by Markem®, Keene, N.Y.; the Artistri® P5000+Series-Pigment Ink sold by Dupont®, or the Epoxy Acrylate Ink, Product No. 00-988, Rahn USA Corp.). The DNA taggant is picked up by swabbing with an MEK soaked cotton tipped applicator and then the DNA is authenticated using a PCR-based analysis method.

The full scope of the invention will be appreciated in view of the U.S. Patents and references cited in this specification, the entire disclosures if which are hereby incorporated by reference.

Having described exemplary embodiments of the present invention, it is further noted that it will be readily apparent to those of reasonable skill in the art that various modifications may be made without departing from the spirit and scope of the invention which is defined by the metes and bounds of the appended claims.

What is claimed is:

1. A method for authenticating an object, comprising:
   providing an object having a coating comprising a taggant, a perturbant and a polymer;
   wherein the taggant comprises a nucleic acid;
   wherein the perturbant comprises: (i) one or both of a polyol and surfactant; and (ii) one or both of a hydroxypropyl starch and a pyrrolidone compound;
   wherein the polymer comprises one or more of a polyurethane, a shelac, a lacquer, an acrylic compound and an epoxy-based compound;
   recovering the taggant from the object; and
   verifying the authenticity of the object by identifying the taggant.

2. The method of claim 1, wherein the nucleic acid taggant comprises DNA.

3. The method of claim 2, wherein the taggant further includes one or more of an upconverting phosphor (UCP), a UV fluorophore, a ceramic IR marker, an amino acid, a protein, a pheromone, a scent, a trace element and a rare earth element.

4. The method of claim 3, wherein the taggant consists essentially of DNA and one or both of an IR upconverting phosphor (UCP) and a UV fluorophore.

5. The method of claim 2, wherein the DNA taggant recovered from the object is authenticated using a method comprising PCR or FISH.

6. The method according to claim 5, wherein the DNA taggant is authenticated in a PCR reaction using primers specific to the DNA taggant to produce specific amplicons, and is identified based on the number of the specific amplicons and the length of each of the specific amplicons amplified in the polymerase chain reaction.

7. The method of claim 1, wherein the perturbant consists essentially of a polyol, a hydroxypropyl starch, and a pyrrolidone compound.

8. The method of claim 7, wherein the polyol of the perturbant comprises polyethylene glycol (PEG), polypropylene glycol, or a mixture of polyethylene glycol (PEG) and polypropylene glycol.

9. The method of claim 8, wherein the polyol of the perturbant comprises one or both of PEG 200 and PEG 10,000.

10. The method of claim 1, wherein the at least one polyol is selected from the group consisting of ethylene glycol, diethylene glycol, triethylene glycol, propylene glycol, polyethylene glycol, and polypropylene glycol.

11. The method of claim 1, wherein the perturbant is in a range from about 0.1% w/w to about 30% w/w of the polymer.

12. The method of claim 11, wherein the perturbant is in a range from about 1% w/w to about 20% w/w of the polymer.

13. The method of claim 12, wherein the perturbant is in a range from about 1% w/w to about 10% w/w of the polymer.

14. A method for authenticating an object, comprising:
   providing an object having a coating comprising a taggant, a perturbant and a polymer;
   wherein the taggant comprises a nucleic acid;

wherein the perturbant comprises: (i) one or both of a polyol and surfactant; and (ii) one or both of a hydroxypropyl starch and a pyrrolidone compound;

wherein the polymer comprises one or more selected from the group consisting of epoxyacrylate, epoxyurethane, polycarbonate (PC), polymethyl methacrylate (PMMA), polyurethane (PU), polystyrene (PS), polyamide, polypropylene (PP), polyvinyl chloride (PVC), polysulphone, polyvinylacetate (PVA), polyester (PES), polyethylene terephthalate (PET), polyethylene (PE), benzocyclobutene (BCB), high-density polyethylene (HDPE), polyvinylidene chloride (PVDC), low-density polyethylene (LDPE), high impact polystyrene (HIPS), acrylonitrile butadiene styrene (ABS), phenol-formaldehyde resins (PF), melamine formaldehyde (MF), polyetheretherketone (PEEK), polyetherimide (PEI), polyimide, polyether imide, polyether ketone imide, polylactic acid (PLA), polytetrafluoroethylene (PTFE), polymethyl pentene, polyether ketone, polyether sulphone, polyphenylene sulfide, polytetrafluoroethylene, butyl rubber, fluropolymers, silicones, ionomers, moldable elastomers, ethylene vinyl alcohol (EVOH), metallocene polymers and polyethylene naphthalate;

recovering the taggant from the object; and verifying the authenticity of the object by identifying the taggant.

15. The method of claim 14, wherein the nucleic acid taggant comprises DNA and the DNA recovered from the object is authenticated using a method comprising PCR or FISH.

16. The method of claim 14, wherein the perturbant is in a range from about 0.1% w/w to about 30% w/w of the polymer.

17. An object marked with a taggant comprising a coating comprising a taggant, a perturbant, and a polymer;

wherein the taggant comprises a nucleic acid;

wherein the perturbant comprises: one or both of a hydroxypropyl starch and a pyrrolidone compound;

wherein the perturbant further comprises: one or both of a polyol and surfactant; and wherein the polymer comprises one or more of a polyurethane, a shelac, a lacquer, an acrylic compound and an epoxy-based compound.

18. The object of claim 17, wherein the polyol of the perturbant comprises polyethylene glycol (PEG), polypropylene glycol, or a mixture of polyethylene glycol (PEG) and polypropylene glycol.

19. The object of claim 18, wherein the polyol of the perturbant comprises one or both of PEG 200 and PEG 10,000.

* * * * *